United States Patent [19]

van't Hooft et al.

[11] Patent Number: 4,861,520

[45] Date of Patent: Aug. 29, 1989

[54] CAPSULE FOR RADIOACTIVE SOURCE

[75] Inventors: Eric van't Hooft, Gezichtslaan 16, 3956 BB Leersum; Libbe van Zwol, Leersum, both of Netherlands

[73] Assignee: Eric van't Hooft, Netherlands

[21] Appl. No.: 263,848

[22] Filed: Oct. 28, 1988

[51] Int. Cl.[4] ............ G21G 4/00; C09K 11/00; A61F 2/66

[52] U.S. Cl. .................. 252/644; 128/654; 128/656; 128/658; 128/659; 252/645; 600/2; 600/4; 600/7; 600/8; 604/891.1; 604/52

[58] Field of Search ............ 424/1.1; 252/633, 628, 252/644, 645, 302, 308; 250/506.1, 507.1; 128/654, 656, 658, 659; 600/1, 2, 4, 7, 8; 604/891.1, 52, 21, 53, 93

[56] References Cited

U.S. PATENT DOCUMENTS

| | | | |
|---|---|---|---|
| 2,830,190 | 4/1958 | Karp | 252/644 |
| 3,145,181 | 8/1964 | Courtois et al. | 252/645 |
| 3,154,501 | 10/1964 | Hertz | 252/644 |
| 3,351,049 | 11/1967 | Lawrence | 128/1.2 |
| 3,600,586 | 8/1971 | Barthelemy | 424/1.1 |
| 3,632,520 | 1/1972 | Garber | 252/644 |
| 3,659,107 | 4/1972 | Selle et al. | 250/506.1 |
| 4,323,055 | 4/1982 | Kubitowicz | 424/1.1 |
| 4,562,001 | 12/1985 | Vietake et al. | 250/506.1 |
| 4,654,171 | 3/1987 | Boncoeur et al. | 252/633 |
| 4,726,916 | 2/1988 | Aubert et al. | 252/629 |

OTHER PUBLICATIONS

Ling et al. 1983. *Physical Dosimetry of $^{125}I$ Seeds of a New Design for Interstitial Implant.* Int. J. Radiation Oncology Biol. Phys. vol. 9, pp. 1747–1752.

Primary Examiner—Howard J. Locker
Attorney, Agent, or Firm—Griffin, Branigan & Butler

[57] ABSTRACT

A drivable radioactive source capsule is provided which comprises a tubular body containing therein a plurality of radioactive sources. The said tubular body has a first end and a second end which is a terminus of the tubular body. A plug has an elongated closure portion with the diameter of the closure portion being substantially equal to the inside diameter of said tubular body. The closure portion is disposed within the tubular body through the second end thereof and is attached to the second end of the tubular body. The plug has a connection portion adjacent the closure portion with the diameter of the connecting portion being substantially equal to the outside diameter of the tubular body. An elongated flexible drive cable is connected to the connection portion of the plug. By this arrangement, radioactive sources may be placed in the tubular body and the body is closed by disposing the closure portion of the plug into the second end of the tubular body and attaching the closure portion to the second end of the tubular body.

15 Claims, 1 Drawing Sheet

CAPSULE FOR RADIOACTIVE SOURCE

The present invention relates to a capsule for radioactive sources, and more particularly to such capsule which is drivable by way of a flexible cable from one point to another point.

BACKGROUND OF THE INVENTION

Radioactive sources are used in the art for both diagnosis and treatment of patients, especially human patients Such radioactive sources for such use are normally contained in a "safe" which avoids radiation hazard to technicians or physicians using the radioactive source in a diagnostic or treatment application. However, when the source is to be deployed, for example, in a human patient, the radioactive source must be driven from the safe to the place of diagnosis or treatment in the patient. To this end, the radioactive source is normally contained in a capsule and that capsule is attached to a drive member, most usually a flexible cable, so that the capsule and cable may be driven through a tubular guide from the safe to the point of disposition in the patient. This technique is referred to in the art as brachy therapy, e.g. intracavitary, intralumenal and interstitial radiotherapy, and this technique has become of increased importance in the treatment of certain diseases, especially cancer, in that the radiotherapy can be administered to very localized human body areas, as opposed to broad beam radiotherapy. To achieve this localized radiotherapy, the radioactive source must be placed in close proximity to the tissue being treated, since the radioactive source emits low levels of radiation at a distance from the locus of therapy and only high levels at the locus of therapy (the inverse square of the distance law). Thus, the application of the radiotherapy is normally achieved by guiding a radioactive source through at least one tubular guide until that source reaches the site of the tissue to be treated, e.g. cancerous tissue. A regiment of radiation is then administered according to a program defined for the particular cancerous tissue, and the therapy is, usually, periodically repeated until effective control of the cancerous tissue is achieved Since repeated treatments may be required, it is important that the technician or physician administering the treatment not be in close proximity to the patient during treatment, since the radioactive source, while emitting low levels of radiation at a distance from the source, emits high levels of radiation near the source, and over a period of time and with numerous patients this can result in dangerous total radiation to the technician or physician. To avoid such radiation hazard to the technician or physician, apparatus has been developed so that the radioactive source is not moved from the safe until the apparatus is fully in place on the patient and the technician or physician is not in close proximity to the patient during treatment, e.g. in a separate room. Such apparatus is known in the art as remote after loading apparatus for brachy therapy, e.g. intracavitary, intralumenal and interstitial radiotherapy. For example, when using such apparatus, a technician interstitially places a positioning member, e.g. a needle or canula at the site where radiotherapy is to be effected. This positioning member is then attached to one end of a tubular guide, and the tubular guide is attached at the other end thereof to a connection head of the remote after loading apparatus. After such positioning and connections are made, a technician, from a remote location, e.g. another room, can cause the apparatus to drive a cable with the radioactive source contained in a capsule attached to the cable from the safe, through the remote after loading apparatus, the tubular guide and into the positioning member for radiotherapy. Thus, the technician will not be in close proximity to the patient while the radioactive source is out of the safe and while administering the therapy.

While apparatus of the above nature has been used for some time, a particular problem in connection therewith has been the ability of the capsule containing the radioactive source to be driven through the apparatus, especially the tubular guide, when that tubular guide is disposed in a tortuous path. The capsule, for safety reasons, must ensure that the radioactive source or sources contained therein are not dislodged from the capsule either while in the after loading apparatus or while passing through the tubular guide or while in the patient. To this end, the capsules are made of metal, and the radioactive source or sources are sealed in the metal capsule, usually by welding, to ensure that no dislodging of the radioactive sources will take place. Since the capsule is made of metal, the capsule is rigid, and when the capsule encounters a tortuous turn in the tubular guide, or other parts of the apparatus or in the patient, the capsule may not be able to traverse that tortuous turn and becomes lodged. As can be appreciated from the foregoing, it is therefore important that the length of the rigid capsule be as short as possible. Typically, the internal diameter of the tubular guide will only be about 1.5 millimeters or less and, consequently, the diameter of the capsule must be about 1.5 millimeters or less, usually about 1.1 millimeters. The capsules most often contain one or a plurality of radioactive sources, e.g. 4, 5, 6, 7, 8 or even 10 or more, and the length of the capsule is correspondingly increased with the number of sources. A typical capsule, containing seven radioactive sources, will have an overall length of approximately 7.2 millimeters. When a capsule of that length encounters a tortuous turn, e.g. in the tubular guide, the chances of the capsule binding in that turn significantly increases.

As can be appreciated from the foregoing, even small deviations in the length of the capsule significantly affect the ability of the capsule to traverse such tortuous turns.

In the usual and known method of manufacturing source capsules, a flexible transport cable is attached to the back end of the capsule. The front end of the capsule is open so that the required radioactive source or numbers of sources may be placed into the capsule. Thereafter, the front end of the capsule is sealed by inserting a rounded plug into the front end of the capsule, and that plug is then attached to the capsule, usually by welding. However, in such a welding operation, the plug must be held in position for welding by a holder having a pair of tongs or grippers with the result that the plug must have a certain minimum length in order to be securely held by such holder during the welding operation. In addition, the attachment, e.g. weld, is tested by a strong axial pull on the plug and the apparatus for gripping the plug for such pull test requires a plug of substantial relative length, e.g. about a minimum of 1.35 millimeters. As can be appreciated, this pull test is necessary in order to insure that the plug is well attached to the capsule, since if the plug dislodged from the capsule and allowed the source or sources to be lost in the apparatus, or much worse in the patient, disastrous results would ensue Consequently, the overall length of the capsule, with the plug attached, is increased beyond that necessary for the capsule containing the radioactive sources, and this increased length increases the chances of the capsule binding in the tubular guide or other parts of the apparatus during an attempted traverse of a tortuous turn.

As can, therefore, be appreciated, it would be a substantial advantage to the art to provide a capsule which can contain the same number of radioactive sources as known capsules, but which capsule is of a significantly shorter length than the known capsules

BRIEF DESCRIPTION OF THE INVENTION

The present invention is based on three major discoveries and several subsidiary discoveries. First of all, it was found that if the capsule, in the form of a tubular body, is manufactured with the front end thereof in an appropriate configuration, e.g. a rounded configuration, then the necessity for providing the elongated plug at the front end for welding to the tubular body could simply be eliminated. By eliminating this welding step, the necessity for an increased length of the plug, as in the prior art devices, is also eliminated, since there is no requirement for the plug having a length adequate for holding by the holder during the welding process or adequate in length for a pull test, as described above.

A second important discovery is that the welding to close the capsule in the form of a tubular body can take place at the back end of the tubular body. In this regard, a plug can be inserted into the back end of the tubular body, but if that plug is previously attached to the flexible drive cable, then the combination of the plug and drive cable provides far more than adequate length for securing in a holder during the welding operation and performing the pull test.

Further, it has been found that when the tubular body has a uniformly shaped end, e.g. a rounded end, this provides a much more uniform field of radiation along the length of the capsule, since the relatively massive plug of the prior art is eliminated and therewith the radiation shielding which it effected.

Also, it would be found that weldings of the present capsule could take place, very conveniently and very predictably, by use of laser or electron-beam welding and that such welding techniques, in combination with the source capsule, produced very predictably sealed capsules.

Thus, the invention provides a drivable radioactive source capsule comprising a tubular body containing therein one or more radioactive sources. The tubular body has a first end (closed end), preferably a rounded first end, and a second end which is a terminus of the tubular body. A plug having an elongated closure portion with the diameter of the closure portion being substantially equal to the inside diameter of the tubular body is disposed within the tubular body such that the closure portion is passed through the second end of the tubular body and attached to the second end of the tubular body. The plug also has a connection portion adjacent the closure with the diameter of the connection portion being substantially equal to the outside diameter of the tubular body. An elongated flexible drive cable is connected to the connection portion of the plug. By this arrangement, radioactive sources may be placed in the tubular body and the tubular body is closed by disposing the closure of the plug into the second end of the tubular body and attaching the closure to the second end of the tubular body.

DETAILED DESCRIPTION OF THE INVENTION

Figure 1:
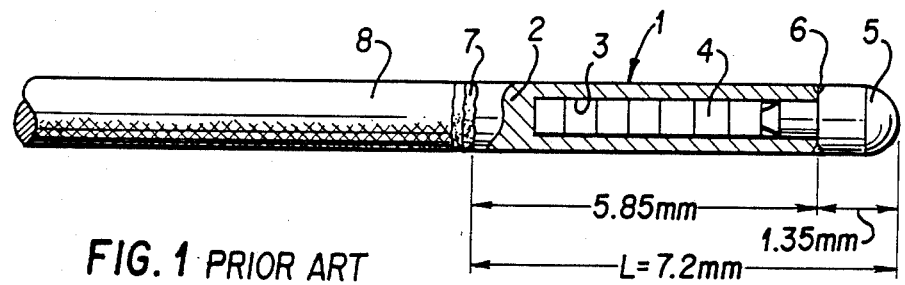
FIG. 1 is a partial cross-section of known prior art source capsules having a flexible drive cable attached thereto.
Figures 4, 5:
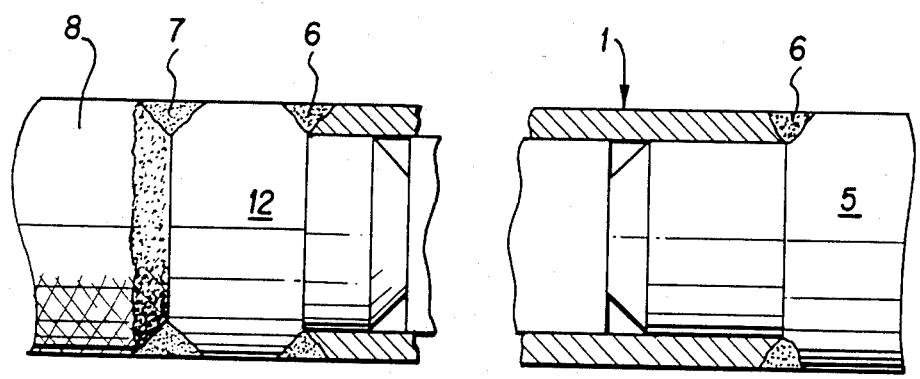
FIG. 4 is a detail of FIG. 2.
FIG. 5 is a detail of FIG. 1.

The known prior art source capsules can be best understood from FIG. 1, which shows a typical example thereof. The source capsule is composed of a tubular body 1 having a closed back end 2 and a cavity 3 for receiving and containing one or a plurality of radioactive sources 4, seven of which are shown in FIG. 1. The sources 4 are sealed in cavity 3 by plug 5 which, as shown in FIG. 5, is usually attached to tubular body 1 by a weld 6. Tubular body 1, in turn, is attached to a flexible cable 8 by means of a further weld 7. In such prior art devices, as shown in FIG. 1, the tubular body 1 has a typical length of 5.8 millimeters and the plug 5 has a typical length of 1.35 millimeters, the length of the plug being necessary to secure the plug in a holder during welding and performing the pull test, as explained above. Thus, the overall length of the capsule is 7.2 millimeters, apart from weld 7.

Figure 2:
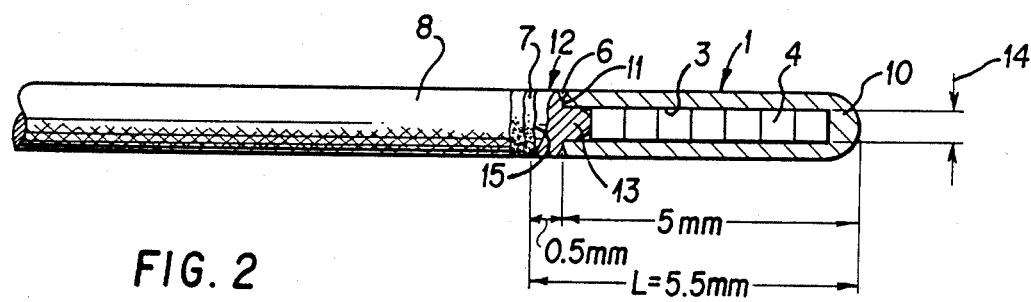
FIG. 2 is a partial cross-section of the source capsule according to the present invention having a flexible drive cable attached thereto.

Turning now to FIG. 2, which shows an embodiment of the present invention, the drivable radioactive source capsule of the present invention comprises a similar tubular body 1 having a similar cavity 3, but having a first end 10, which is preferably rounded as shown, formed thereon. By having such a rounded first end 10, as opposed to the plug 5 of the prior art (see FIG. 1), the first end of the capsule is much shorter than the front end of the prior art device containing the plug. This not only shortens the capsule, as noted above, but most desirably, locates the radioactive sources more near the front end of the capsule. This allows more accurate placement of the radioactive sources in the tissues being treated. Further, the entire metal walls and end of the capsule act as radiation shields. As shown in FIG. 1, the relatively massive plug 5 effects much greater shielding than the walls of the capsule. This results in a "dimple" in the isodose of radiation (the radiation dosage with respect to distance from the surfaces of the capsule). By eliminating the plug 5, the present rounded end does not effect a significant "dimple". Elimination of such "dimples" is especially important when using low energy-long wave length isotopes, such as $Ir^{137}$, as opposed to higher energy sources such as cobalt 60.

Tubular body 1 also has a second end 11 which is the terminus of the tubular body, as shown in Figure 2. As opposed to the prior art, the present invention provides a plug 12 having an elongated closure portion 13 with the diameter of the closure portion being substantially equal to the inside diameter (shown by arrows 14) of the tubular body 1. It will be appreciated in this regard that the term "substantially equal" means that the diameter of the elongated closure portion 13 is close to but slightly less than the inside diameter of tubular body 1, so that the closure portion 13 may be snugly fitted into tubular body 1.

As can also be seen from FIG. 2, the closure portion 13 is of a sufficient length that it can be accurately placed in tubular body and will snugly contain the precise numbers of sources in the capsule such that the sources are not free to move within the capsule during use of the capsule. Of course, the radioactive sources will normally have a diameter essentially equal to (but slightly less than) the inside diameter of tubular body 1.

Plug 12 also has a connection portion 15 disposed adjacent to the closure portion and forming a unitary plug. The diameter of the connection portion 15 is substantially equal to the outside diameter of the tubular body 1 and, also, preferably is substantially equal to the diameter of the drive cable 8. Thus, preferably the diameters of the drive cable 8, the plug 12 and the tubular body 1 are all substantially equal, so that the combination of the drive cable and capsule may be passed through a tubular guide for correctly disposing the capsule, with the radioactive sources therein, in the patient being treated. This is also preferred since if the diameter of the cable is substantially less than the diameter of the capsule, e.g. one-third less, (and, hence, also substantially less than the internal diameter of the tubular guide), the cable can bend or "snake" within the tubular guide during movement therethrough. This can result in not only binding of the cable, but also result in the cable actually moving the capsule a shorter distance through the tubular guide than would be indicated by the actual length of the cable having been driven from the head of the after loading apparatus. This could give a false indication as to the final position of the capsule in the patient being treated.

Elongated flexible drive cable 8 is connected to the connection portion 15 of the plug 12 prior to assembly of the tubular body 1 to plug 12. By this arrangement, the radioactive sources 4 may be placed in the tubular body 1 through the opened second end 11, and the tubular body 1 is closed by disposing the closure portion 13 of plug 12 into the second end 11 of the tubular body 1 and attaching the closure portion 13 to the second end 11 of the tubular body 1.

As noted above, the capsule is normally attached to the drive cable by welding. In the present invention, the drive cable 8 is welded to the connection portion 15 of plug 12 prior to closing tubular body 1 by plug 12. Thus, tongs or other similar holding devices can easily grip the combination of plug 12 and drive cable 8 for accurately placing plug 12 into tubular body 1, welding plug 12 thereto and performing the required pull test. By this arrangement, as opposed to the prior art, there is no need for an elongated plug, which elongated plug substantially increases the overall length of the capsule and adversely effected the isodose line, as explained above. Further, the radioactive sources are contained within the tubular body 1 between the first end 10 and the closure portion 13 of plug 12 so that the radioactive sources are very snugly held within the capsule. After such assembly, the closure portion 13 of plug 12 is attached to the second end 11 of tubular body 1 in any manner desired, but most often this attachment will be by a weld, as in the prior art. However, as noted above, that weld can be easily achieved without the necessity of the extended plug, which was required in the prior art.

It has been found in this latter regard, that the weld of the closure portion 13 to the second end 11 is most advantageously carried out when the weld is an electron-beam weld. While electron-beam welding is well known in the art and the details thereof need not be set forth herein for sake of conciseness, with electron-beam welding, weld 6 (see FIG. 4) can very accurately and precisely attach closure portion 13 to second end 11 of tubular body 1. As can be appreciated, the welding of plug 12 to tubular body 1 must be a very accurate weld in order to ensure that plug 12 is fully seated in tubular body 1 and that the attachment of plug 12 to tubular body 1 is quite secure in order to avoid radiation source leakage or dislodgment of the plug, for the reasons explained above.

Also, drive cable 8 can be attached to connecting portion 15 of plug 12 in any desired manner, but it is far preferable that that attachment be by means of a weld. However, in this case, it is preferred that the weld is a laser weld. Again, laser welding is well known in the art and need not be described herein for conciseness purposes, but laser welding has been found to be most effective in attaching the flexible drive cable (usually made of steel) to the connecting portion 15 of plug 12. It has been found that laser welding ensures a good connection of cable 8 to plug 12 so that no separation thereof occurs even when the cable and capsule are passed through tortuous turns in the tubular guide.

In regard to the method of producing the capsule of the present invention, it is only necessary to provide the tubular body 1 having the rounded end 10. Means of producing such tubular bodies are well known in the art and need not be described herein. The tubular bodies are normally made of steel or like rigid metal material and can be formed by conventional machining techniques. The plug 12 preferably is machined, but it can be formed by a die casting technique, both of which processes are well known in the art. The flexible drive cable is then attached to the connection portion 15 of plug 12, preferably by welding as described above. A plurality of radioactive sources are then placed in tubular body 1 through second end 11. The closure portion 13 of plug 12 is then disposed within the tubular body through the second end 11. Thereafter, the closure portion 13 is attached to the second end 11, preferably by welding as described above. Preferably, the wires of cable 8 are first welded together to form a solid end and then simply butt welded to connection portion 15. However, if desired, a thread may be formed on the solid welded end of cable 8. The connection portion 15 may also be internally threaded (not shown in the drawings) and the threaded solid end of cable 8 is threaded into the internal threads of connection portion 15 and then welded, as described above.

As shown in FIG. 2, with the present arrangement, the same number of sources, i.e. 7 sources, can be contained in a capsule with an overall length of 5 millimeters, as opposed to the overall length of 5.85 millimeters in the prior art capsules. Further, since the present plug 12 being previously attached to cable 8 can be much shorter than the prior art plug 5, the overall length of the capsule and plug of the present invention, as shown in FIG. 2, can be 5.5 millimeters, as opposed to the overall length of 7.2 millimeters with plugs of the prior art. This results in a shortening of the overall length of the capsule by 1.7 millimeters. While this shortening may seem quite small, that amount of shortening provides considerable advantages in passing the rigid capsule through a tortuous turn of, for example, a tubular guide and is a decided advantage in the art. In addition, the present rounded end provides a much more desirable isodose line, as explained above.

Figure 3:
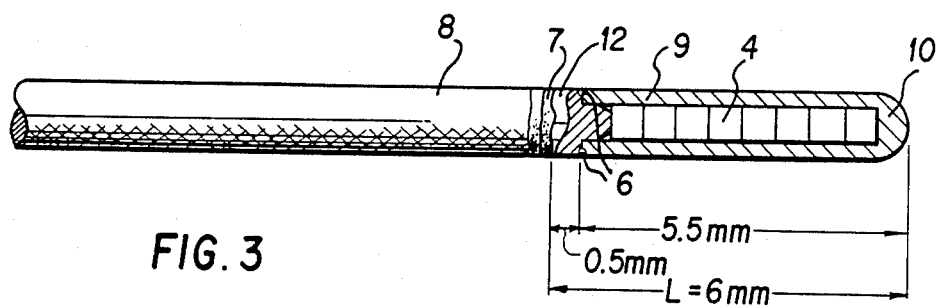
FIG. 3 is similar to FIG. 2, but shows the source capsule of the present invention attached to a flexible drive cable, with additional sources in the source capsule.

FIG. 3 shows an embodiment similar to FIG. 2, but where the capsule contains eight radioactive sources. Again, it will be seen that the overall length is 6 millimeters, as opposed to the prior art capsule containing only seven sources and having an overall length of 7.2 millimeters. Thus, with the present invention, an additional source can be added to the capsule, while at the same time, substantially shortening the capsule, as opposed to prior art capsules.

It will be apparent to those skilled in the art that modifications of the above-described invention can be easily appreciated, and it is intended that those modifications being included- .within the spirit and scope of the annexed claims.

What is claimed is:

1. A drivable radioactive source capsule comprising:
   (1) a tubular body containing therein one or more radioactive sources, said tubular body having a first end and a second end which is a terminus of the tubular body;
   (2) a plug having an elongated closure portion with the diameter of said closure portion being substantially equal to the inside diameter of said tubular body, said closure portion being disposed within the tubular body through the second end thereof and being attached to said second end of the tubular body, and said plug having a connection portion adjacent said closure portion with the diameter of the connecting portion being substantially equal to the outside diameter of the tubular body: and
   (3) an elongated flexible drive cable connected to said connection portion of said plug;
   whereby radioactive sources may be placed in said tubular body and said body closed by disposing the closure portion of the plug into the second end of the tubular body and attaching the closure portion to the second end of the tubular body.

2. The capsule of claim 1 wherein the said drive cable is welded to said connection portion of said plug.

3. The capsule of claim 1 wherein the said first end is rounded and the said radioactive sources are contained within said tubular body between said first end of the tubular body and the closure portion of said plug.

4. The capsule of claim 1 wherein the closure portion of the said plug is attached to the second end of the tubular body by a weld.

5. The capsule of claim 4 wherein the weld is an electron-beam weld.

6. The capsule of claim 1 wherein the drive cable is attached to the connection portion of said plug by a weld.

7. The capsule of claim 6 wherein the weld is a laser weld.

8. The capsule of claim 1 wherein the diameters of the tubular body, plug and cable are substantially the same.

9. A method of producing the capsule of claim 1 comprising
   (1) providing said tubular body;
   (2) attaching said flexible drive cable to said connection portion of said plug;
   (3) placing a plurality of radioactive sources in said tubular body through said second end thereof;
   (4) disposing said closure portion of said plug within the tubular body through the second end thereof; and
   (5) attaching the closure portion to said second end.

10. The method of claim 9 wherein the said drive cable is attached to the said connection portion by welding.

11. The method of claim 10 wherein said welding is by laser welding.

12. The method of claim 9 wherein the closure portion of the said plug is attached to the second end of the tubular body by welding.

13. The method of claim 12 wherein the welding is by electron-beam welding.

14. The method of claim 9 wherein the end flexible drive cable is welded to a solid end, a thread is formed on the solid end and the threaded solid end is threaded into the connection portion of said plug.

15. The method of claim 9 wherein the diameters of the tubular body, plug and cable are substantially the same and the said first end of the tubular body is rounded.

* * * * *